United States Patent
Hashemi et al.

(10) Patent No.: US 12,012,609 B2
(45) Date of Patent: Jun. 18, 2024

(54) CONDUCTIVE GRAPHENE MATRIX-ENCAPSULATED CELLS

(71) Applicant: Iowa State University Research Foundation, Inc., Ames, IA (US)

(72) Inventors: Nicole Nastaran Hashemi, Ames, IA (US); Reza Montazami, Ames, IA (US); Marilyn Christine McNamara, Ames, IA (US); Jasmin Okuzono, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 18/195,017

(22) Filed: May 9, 2023

(65) Prior Publication Data
US 2023/0272335 A1    Aug. 31, 2023

Related U.S. Application Data

(62) Division of application No. 16/716,250, filed on Dec. 16, 2019, now Pat. No. 11,680,243.

(60) Provisional application No. 62/808,018, filed on Feb. 20, 2019.

(51) Int. Cl.
| | | |
|---|---|---|
| *C12N 5/00* | (2006.01) | |
| *B82Y 15/00* | (2011.01) | |
| *B82Y 40/00* | (2011.01) | |
| *C01B 32/19* | (2017.01) | |
| *C08J 5/00* | (2006.01) | |

(52) U.S. Cl.
CPC ............ *C12N 5/0012* (2013.01); *B82Y 15/00* (2013.01); *C01B 32/19* (2017.08); *C08J 5/005* (2013.01); *B82Y 40/00* (2013.01)

(58) Field of Classification Search
CPC ......... B82Y 15/00; B82Y 40/00; C01B 32/19; C08J 5/005; C12N 5/005
USPC .......................................................... 435/382
See application file for complete search history.

(56) References Cited

U.S. PATENT DOCUMENTS

| | | |
|---|---|---|
| 5,656,469 A | 8/1997 | Tresco et al. |
| 2010/0215724 A1* | 8/2010 | Prakash .................. A61K 9/06 977/750 |
| 2015/0064265 A1 | 3/2015 | Fahmy et al. |

(Continued)

FOREIGN PATENT DOCUMENTS

| | | | |
|---|---|---|---|
| CN | 108014849 A | 5/2018 | |
| EP | 3395327 A1 | 10/2018 | |
| WO | WO-2017049021 A1 * | 3/2017 | ............ B82Y 30/00 |

OTHER PUBLICATIONS

Wang "Synthesis of Biomaterials Utilizing Microfluidic Technology." Genes 2018, 9, 283; doi:10.3390/genes9060283 (Year: 2018).*

(Continued)

*Primary Examiner* — Tri V Nguyen
(74) *Attorney, Agent, or Firm* — Schwegman Lundberg & Woessner, P.A.

(57) ABSTRACT

Various embodiments disclosed relate to conductive graphene matrix-encapsulated cells. A matrix-encapsulated cell includes an encapsulating polymer matrix including a biopolymer and graphene. The matrix-encapsulated cell also includes one or more of the cells encapsulated within the encapsulating polymer, wherein the graphene directly contacts at least some of the cells. The matrix encapsulating the one or more cells is electrically conductive.

18 Claims, 7 Drawing Sheets

(56) References Cited

U.S. PATENT DOCUMENTS

| | | |
|---|---|---|
| 2016/0030631 A1 | 2/2016 | Agarwal et al. |
| 2017/0035943 A1 | 2/2017 | Simon et al. |
| 2020/0263127 A1 | 8/2020 | Hashemi et al. |

OTHER PUBLICATIONS

Veerla "Fabrication of a microfluidic device for studying the in situ drug-loading/release behavior of graphene oxide-encapsulated hydrogel beads." Biomaterials Research, 22, 7 (Year: 2018).*

"U.S. Appl. No. 16/716,250, Non Final Office Action mailed Sep. 16, 2022", 12 pgs.

"U.S. Appl. No. 16/716,250, Notice of Allowance mailed Feb. 7, 2023", 10 pgs.

"U.S. Appl. No. 16/716,250, Response filed Oct. 27, 2022 to Non Final Office Action mailed Sep. 16, 2022", 11 pgs.

"U.S. Appl. No. 16/716,250, Restriction Requirement mailed May 12, 2022", 7 pgs.

Chen, Chuntao, et al., "Electrically-responsive core-shell hybrid microfibers for controlled drug release and cell culture", Acta Biomaterialia, 55, (2017), 434-442.

Ciriza, "Graphene oxide enhances alginate encapsulated cells viability and functionality while not affecting the foreign body response", Drug Delivery 2018, vol. 25, No. 1, (2018), 1147-1160.

Ciriza, "Graphene oxide increases the viability of C2C12 myoblasts microencapsulated in alginate", International Journal of Pharmaceutics 493, (2015), 260-270.

Peng, Li, et al., "Preparation and Characterization of Electro-responsive Graphene Oxide/Hydrolyzed Polyacrylamide/Sodium Alginate Hydrogel Fiber", In: Advanced Functional Materials, (2018), 673-680.

Pham, Quynh P., et al., "Electrospinning of Polymeric Nanofibers for Tissue Engineering Applications: A Review", Tissue Engineering, 12(5), (2006), 1197-1211.

Schirmer, Katharina S. U., et al., "Cell compatible encapsulation of filaments into 3D hydrogels", Biofabrication 8(2): 025013, (2016), 1-13.

Vusa, Chiranjeevi, et al., "Facile and green synthesis of graphene", RSC Advances, 4, (2014), 22470-22475.

Yue, Kan, et al., "Synthesis, properties, and biomedical applications of gelatin methacryloyl (GelMA) hydrogels", Biomaterials, 73, (2015), 254-271.

* cited by examiner

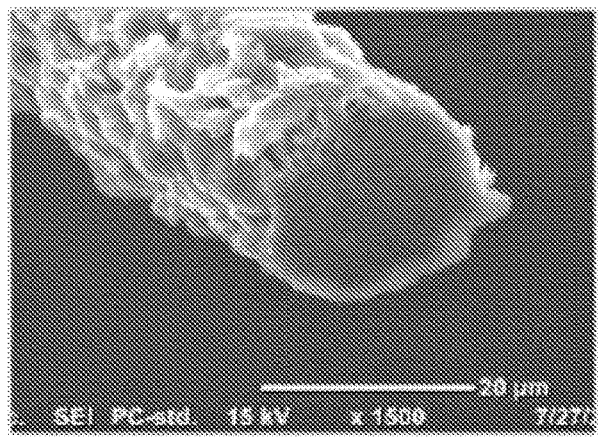 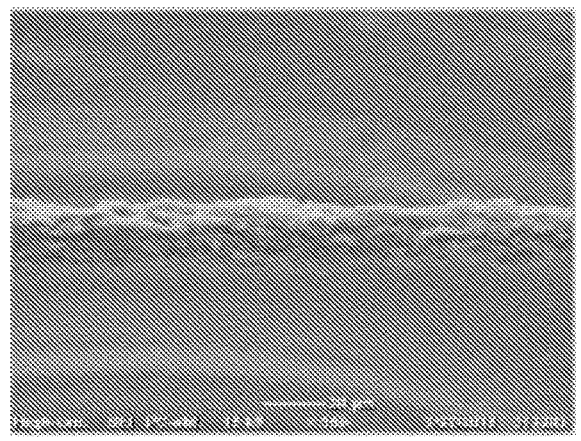
FIG. 2A FIG. 2B
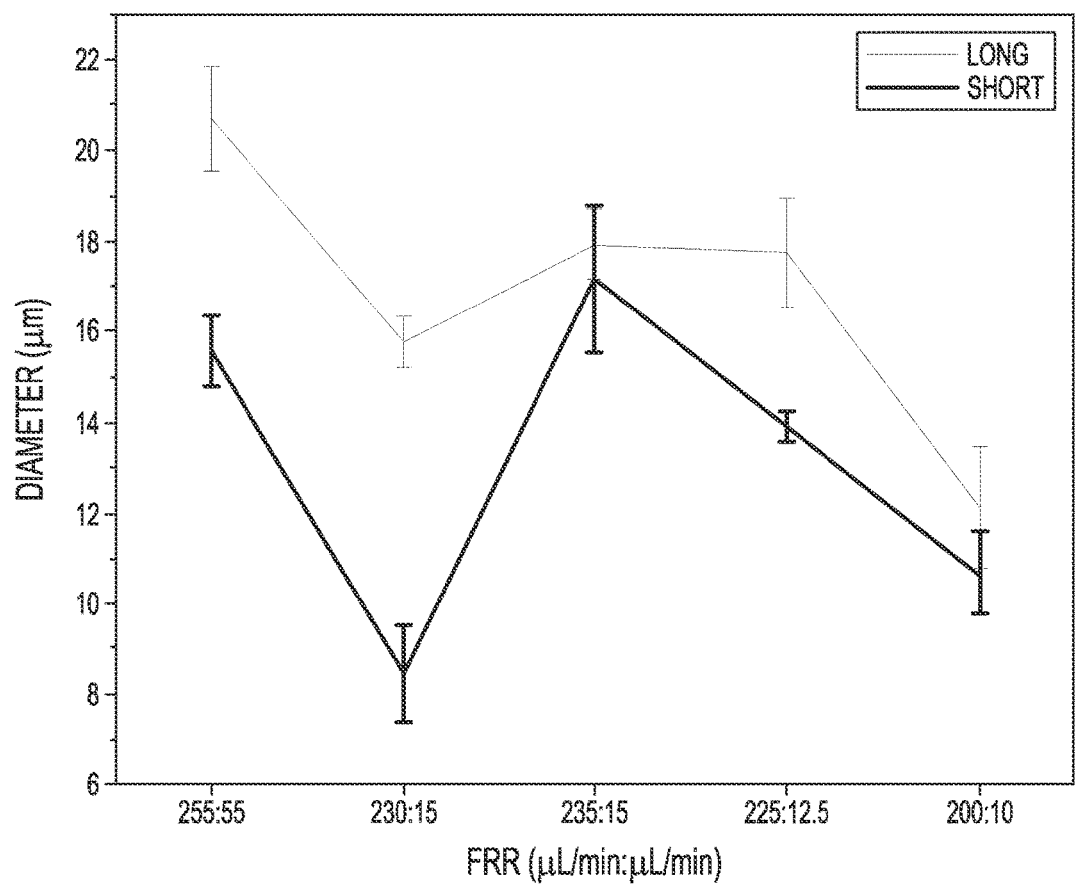
FIG. 3

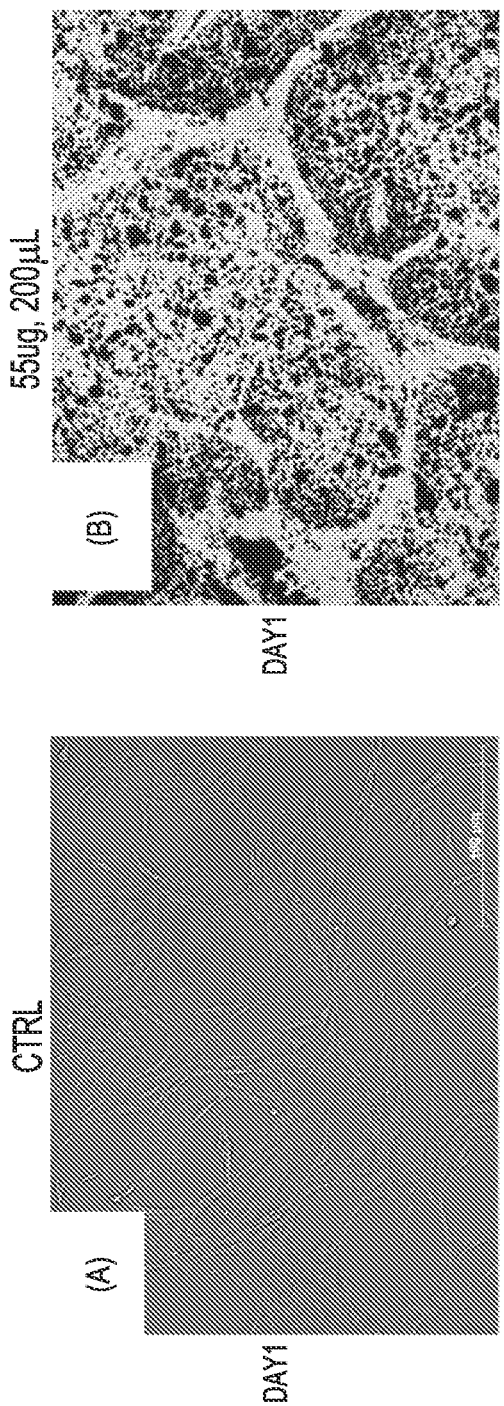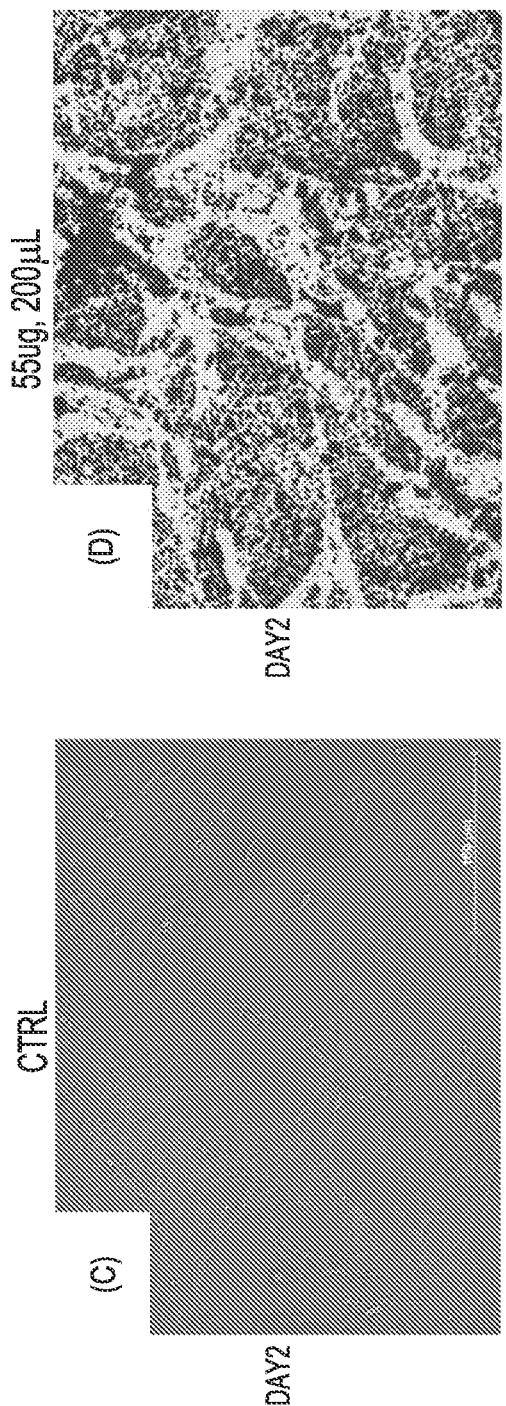
FIG. 4A  FIG. 4B  FIG. 4C  FIG. 4D

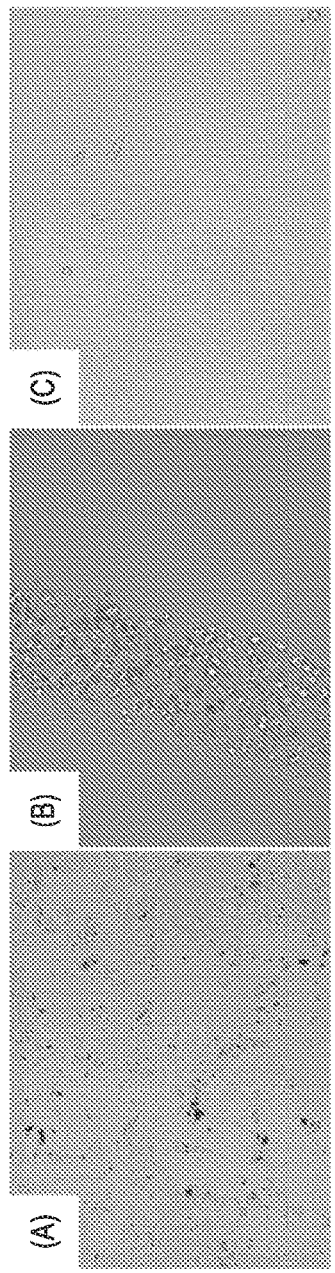
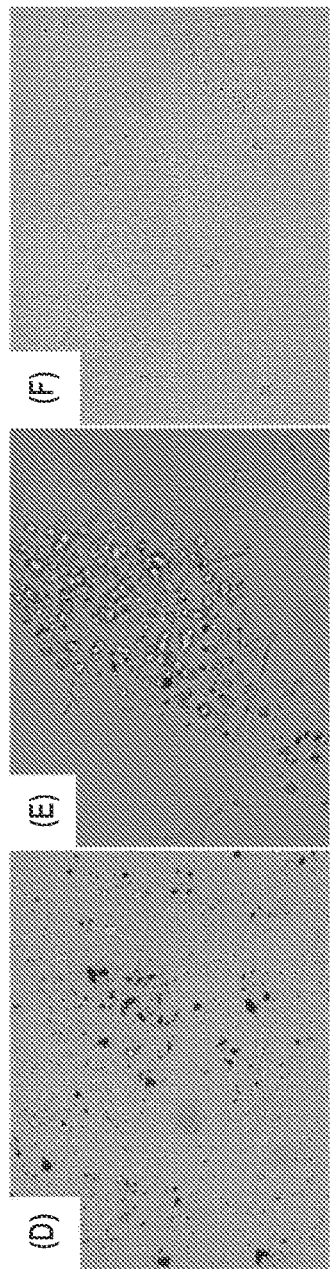
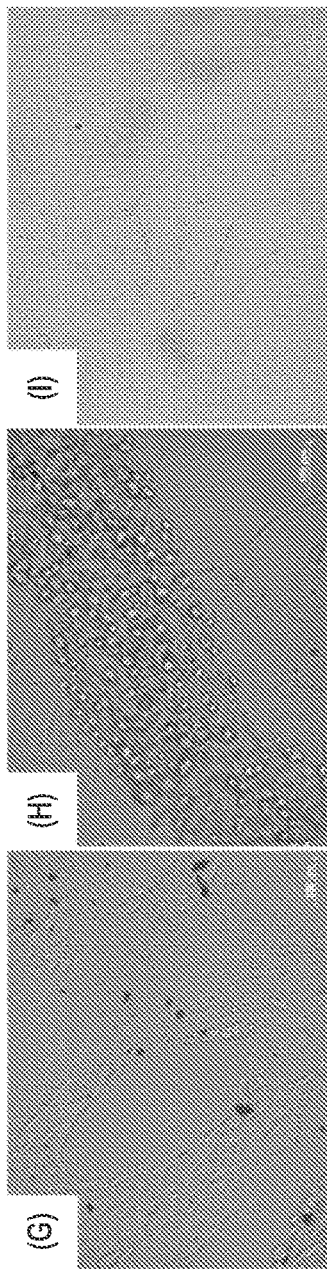

CONDUCTIVE GRAPHENE MATRIX-ENCAPSULATED CELLS

CROSS-REFERENCE TO RELATED APPLICATION

This application is a division of U.S. patent application Ser. No. 16/716,250, filed Dec. 16, 2019, which claims the benefit of priority to U.S. Provisional Patent Application Ser. No. 62/808,018 filed Feb. 20, 2019, the disclosures of which are incorporated herein in their entirety by reference.

STATEMENT OF GOVERNMENT SUPPORT

This invention was made with Government support under N000141612246, N000141712620, and W911NF1710584 awarded by the Department of Defense. The U.S. Government has certain rights in this invention.

BACKGROUND

Hydrogel microfibers have many applications in tissue engineering and regenerative medicine, where they are favored for their physical and chemical properties, as well as their reproducible and cell-safe fabrication methods. A variety of biocompatible polymers are utilized for this method of microfiber creation; among them, alginate is favored within biomedical applications for its good biocompatibility, biodegradability and low toxicity, as well as its capacity for polymerization within mild conditions. These factors have garnered interest for alginate in the realms of cell encapsulation, which requires cells to be present during the gelation of the microfibers, thereby eliminating the possibility of cell loss but requiring cell-safe gelation conditions. Hydrogel scaffolding creates a physiologically relevant platform for studying cell behavior. Existing research has created hydrogels with enhanced conductivity for the purpose of delivering electrical stimulation to study or control cell response, viability, and regeneration potentials; however, conductive biocompatible hydrogels remain underutilized as 3D electro-sensing cell culture scaffoldings.

While there are a range of ways to enhance the conductivity of materials, only some are suitable for biomedical applications. Since its discovery in 2004, graphene has drawn much attention in the fields of nanoscience, and has become known as a functional material in biomedical applications due to its biocompatibility, high conductivity, and mechanical properties, which are preferable to other compounds such as reduced graphene oxide. However, challenges arise when non-toxic aqueous solutions of graphene are required, as is the case when both cells and graphene are encapsulated within a hydrogel.

Chemically, graphite exfoliation to form graphene can be assisted by the inclusion of suitable surfactants, which reduce interfacial tensions to aid in suspension. Unfortunately, due to graphene's hydrophobic nature, water alone is not capable of forming a stable, homogeneous solution, as pristine graphene nanosheets are subject to van der Waals forces and show unwanted aggregation. Surfactants typically used to aid in this are typically highly toxic.

Common mechanical techniques for graphene dispersion involve using sonication, but this method requires additional materials and electrochemical procedures to maintain a stable aqueous graphene solution, which affects the biocompatibility of the resulting graphene solution. Graphene oxide may be reduced either thermally or chemically; however, the desired characteristics of the synthesized graphene may not be easily maintained, and requires extensive use of cytotoxic chemicals and procedures.

SUMMARY OF THE INVENTION

Various embodiments provide a matrix-encapsulated cell. The matrix-encapsulated cell includes an encapsulating polymer matrix including a biopolymer and graphene. The matrix-encapsulated cell also includes one or more of the cells encapsulated within the encapsulating polymer. The graphene directly contacts at least some of the cells. The matrix encapsulating the one or more cells is electrically conductive.

Various embodiments provide a fiber including an encapsulating polymer matrix including a biopolymer and graphene. The fiber also includes one or more cells encapsulated within the encapsulating polymer. The graphene directly contacts at least some of the cells. The matrix encapsulating the one or more cells is electrically conductive.

Various embodiments provide a method of making the matrix-encapsulated cell. The method includes polymerizing a pre-polymer solution, the pre-polymer solution including the one or more cells, the graphene, and a precursor for the biopolymer.

Various embodiments provide a method of using the matrix-encapsulated cell. The method includes detecting electrical signals from or sending electrical signals to the one or more cells through the encapsulating polymer matrix.

Various embodiments provide various advantages over other encapsulated cells, at least some of which are unexpected. For example, in various embodiments, the encapsulated polymer matrix is substantially free of graphite, graphene oxide, or reduced graphene oxide, which can have lower electrical conductivity than graphene. In various embodiments, despite the use of non-conductive hydrogels in the encapsulating matrix, the increased conductivity can allow for the elucidation of electrical cell-to-cell communication mechanisms within neuronal cell cultures. In various embodiments, spatially restricting the location of cells during experiments can enable the long-term study of cell-to-cell communication without risk of cells flaking away. In various embodiments, the matrix-encapsulated cells are a physiologically relevant platform for real-time 3D conductivity measurements, thereby allowing for rapid detection of cells' responses to chemical or mechanical inputs.

In various embodiments, the encapsulated cells can survive the encapsulation without harm and can be maintained in an encapsulated state while alive for extended periods. In various embodiments, the cells can be recovered from the encapsulating matrix in a living and healthy state.

In various embodiments, a microfluidic technique can be used to form the matrix-encapsulated cell. The microfluidic technique can avoid harm to the cells during the encapsulation. The ionic cross-linking microfluidic fiber fabrication technique utilizes an ionic exchange between fluids in laminar flow within microfluidic chambers to create gentle polymerization conditions that can yield tunable microfibers which encapsulate live cells. In various embodiments, the microfluidic technique can be versatile, allowing precise control over the diameter and cross-sectional shape of the microfiber through the ability to vary microchannel device size and geometry, as well as the flow rate ratio (FRR) between the core and sheath fluids. Different flow rate ratios can be used to impact the characteristics of the fibers, affecting their size and shape, as well as their mechanical and electrical properties. The microfluidic fabrication technique can provide gentle polymerization conditions and tunable control over cells' spatio-temporal locations.

In various embodiments, the matrix-encapsulated cell can be in the form of a conductive fiber that encapsulates the one or more cells. Conductive materials in biomedical fields include fibers, fibrous mats formed using electrospinning, and conductive hydrogels. Current conductive hydrogels in biomedical fields take the form of membranes, gels, or films. Conductive microfibers, particularly those which encapsulate the cells they are trying to stimulate or study, have untapped potential in terms of long-term experiments where cell location must be controlled. Microfibers can have the ability to mimic spatially organized 3D environments with controllable cell density for extended periods of time. Cutting-edge breakthroughs in the fabrication of biocompatible and stable aqueous graphene solutions enable the encapsulation of both graphene and cells within the alginate hydrogel, thereby creating a highly powerful real-time sensing platform.

BRIEF DESCRIPTION OF THE FIGURES

The drawings illustrate generally, by way of example, but not by way of limitation, various embodiments of the present invention.

FIGS. 2(A)-(B) illustrate scanning electron microscopy images of fibers formed using a microfluidic technique, in accordance with various embodiments.

FIG. 3 illustrates a plot showing fiber diameter versus flow rate ratio for fibers formed using a microfluidic technique, in accordance with various embodiments.

FIGS. 4(A)-(D) illustrate rat PC12 cells seeded onto 6 well plates observed at (A-B) 24 and (C-D) 48 hours after introduction of 200 μL of 5% Graphene solution, in accordance with various embodiments.

FIGS. 5(A)-(I) illustrate rat PC12 cells in a non-polymerized control of alginate, gelatin, graphene (A, D, G), encapsulated in alginate fibers (B, E, H), and cells which migrated from the hydrogels and attached on the surface of the well plate (C, F, I), in accordance with various embodiments. Day 0 (A-C), day 3 (D-F), and day 7 (G-I).

DETAILED DESCRIPTION OF THE INVENTION

Figure 1:
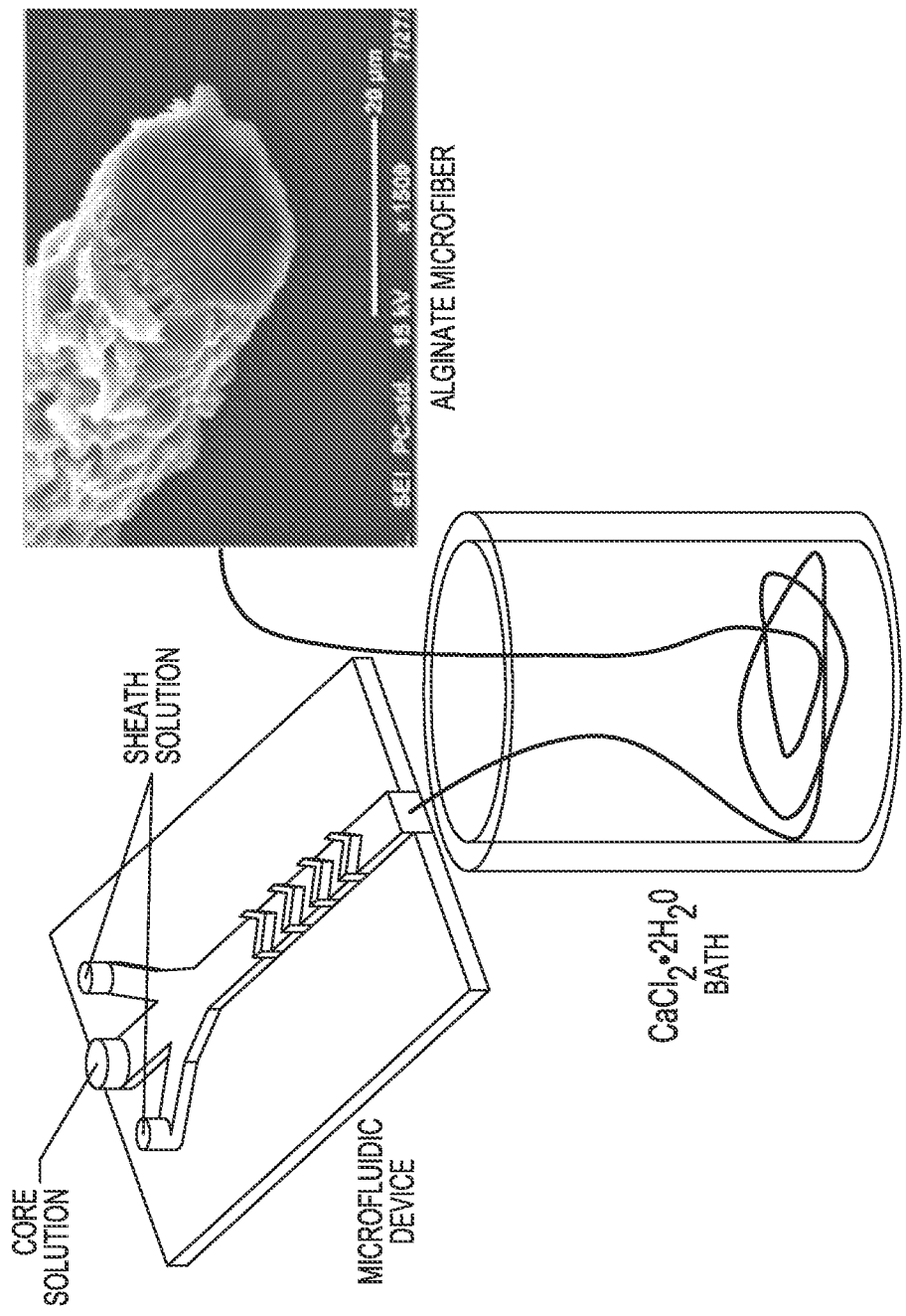
FIG. 1 illustrates a diagram of a microfluidic device used to form fibers, in accordance with various embodiments.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % or mg/mL to about 5 wt % or mg/mL of the composition is the material, or about 0 wt % or mg/mL to about 1 wt % or mg/mL, or about 5 wt % or mg/mL or less, or less than, equal to, or greater than about 4.5 wt % or mg/mL, 4, 3.5, 3, 2.5, 2, 1.5, 1, 0.9, 0.8, 0.7, 0.6, 0.5, 0.4, 0.3, 0.2, 0.1, 0.01, or about 0.001 wt % or mg/mL or less, or about 0 wt % or mg/mL.

As used herein, the term "polymer" refers to a molecule having at least one repeating unit and can include copolymers.

Matrix-Encapsulated Cell

Various embodiments provide a matrix-encapsulated cell. The matrix-encapsulated cell includes an encapsulating polymer matrix that includes a biopolymer and graphene. The matrix-encapsulated cell can also include one or more of the cells encapsulated within the encapsulating polymer. The graphene can directly contact at least some of the cells. The matrix encapsulating the one or more cells can be electrically conductive.

The encapsulating polymer matrix can have any suitable form, such as a membrane, gel, film, fiber, or a combination thereof. In some embodiments, the encapsulating polymer matrix has the form of a fiber. The fiber can have any suitable dimensions, such as length and diameter. As the fibers can be generated via a continuous process, the length is not particularly limited. For example, the fiber can have a length of about 1 micron to about 100 meters, or about 1 cm to about 100 cm, or about 1 cm to about 10 cm. The fiber (e.g., dried fiber) can have a diameter of about 1 micron to about 100 microns, about 2 microns to about 50 microns, or about 10 microns to about 25 microns.

The biopolymer can be any suitable biopolymer, such as gelatin, chitosan, polycaprolactone, a polysaccharide, alginate, or a combination thereof. The biopolymer can include calcium alginate (e.g., alginate crosslinked via calcium ions). The biopolymer can form any suitable proportion of the encapsulating polymer matrix, such as about 0.5 mg/mL to about 10 mg/mL, about 1 mg/mL to about 5 mg/mL, or about 1.5 mg/mL to about 3 mg/mL of the encapsulating polymer matrix. Graphene is a single layer of carbon, while graphite is multiple layers of graphene.

In various embodiments, the graphene is homogenously distributed in the encapsulating polymer matrix. The graphene can provide the electrical conductivity of the encapsulating polymer matrix. The graphene can contact at least some of the cells, and the graphene particles can also contact adjacent graphene particles in the matrix, such that an electrical connection is formed throughout the encapsulating matrix that connects to the contacted one or more cells. In some embodiments, the encapsulating polymer matrix can be substantially free of graphite, graphene oxide (e.g., similar to graphene but having more oxidized groups), reduced oxidized graphene (e.g., a material which is similar to graphene but has more oxidized groups and therefore a different chemical structure), or a combination thereof. The graphene can form any suitable proportion of the combination of the encapsulating polymer matrix and the one or more cells, such as about 5 mg/mL to about 35 mg/mL, about 10 mg/mL to about 25 mg/mL, or about 14 mg/mL to about 18 mg/mL.

The one or more cells can be living cells that can be encapsulated for any suitable time period while still in a living state. In various embodiments, the one or more cells can be recovered from the encapsulating polymer matrix in a living and healthy state. The one or more cells can include any suitable type or variety of cells, such as neural cells, astrocyte cells, or stem cells. The one or more cells can include rat PC12 cells, mouse astrocyte cells (MACs), adult hippocampal progenitor stem cells (AHPCs), or mesenchymal stem cells (MSCs). The one or more cells can include mammalian cells. The one or more cells can include rat PC12 cells. The one or more cells can form any suitable proportion of the combination of the encapsulating polymer matrix and the one or more cells, such as about $1 \times 10^2$ cells/mL to about $1 \times 10^{10}$ cells/mL, about $1 \times 10^4$ cells/mL to about $1 \times 10^8$ cells/mL, about $1 \times 10^5$ cells/mL to about $1 \times 10^7$ cells/mL, or about $1 \times 10^6$ cells/mL to about $5 \times 10^6$ cells/mL.

In some embodiments, the encapsulating matrix further includes gelatin. In some embodiments, the encapsulating matrix is substantially free of gelatin. The gelatin can form any suitable proportion of the encapsulating matrix, such as about 0 mg/mL, or such as about 0.5 mg/mL to about 10 mg/mL, about 1 mg/mL to about 5 mg/mL, or about 1.5 mg/mL to about 3 mg/mL.

The encapsulating matrix can further include a surfactant. The surfactant can be any suitable surfactant, such as Tween (e.g., a polysorbate-type nonionic surfactant formed by the ethoxylation of sorbitan before the addition of lauric acid, such as Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), or Polysorbate 80 (polyoxyethylene (20) sorbitan monooleate)), polyethylene glycol (PEG), or bovine serum albumen (BSA). The surfactant can include bovine serum albumen (BSA).

In some embodiments, the encapsulating matrix can further include solvents in addition to water, such as polyethylene glycol (PEG).

Method of Making the Matrix-Encapsulated Cell

Various embodiments provide a method of making the matrix-encapsulated cells. The method can include polymerizing a pre-polymer solution. The pre-polymer solution can include one or more cells, graphene, and a precursor for the biopolymer. The method can be a microfluidic technique, or can be another technique. The pre-polymer solution can be an aqueous solution.

The graphene can be non-agglomerated and form any suitable proportion of the pre-polymer solution. For example, the graphene can be about 1 mg/mL to about 30 mg/mL, about 10 mg/mL to about 30 mg/mL, about 15 mg/mL to about 25 mg/mL, or about 18 mg/mL to about 22 mg/mL of the pre-polymer solution.

The precursor for the biopolymer can form any suitable proportion of the pre-polymer solution. For example, the precursor for the biopolymer (e.g., alginate) can be about 1 mtg/mL to about 15 mg/mL, about 2 mg/mL to about 8 mg/mL, or about 3 mg/mL to about 5 mg/mL of the pre-polymer solution.

The pre-polymer solution can further include a surfactant to maintain the graphene in a non-agglomerated state during the polymerization. The surfactant can be any suitable surfactant. The surfactant can be about 1 mg/mL to about 20 mg/mL, 5 mg/mL to about 15 mg/mL, or about 8 mg/mL to about 12 mg/mL of the pre-polymer solution. In some embodiments, the surfactant can include Bovine Serum Albumen (BSA). Bovine serum albumen can be used to aid with the dispersion of graphene. BSA is a water-soluble protein which is able to make non-covalent bonds with both positively and negatively charged particles, a feature which aids in the stability, encapsulation efficiency, and release rates in the field of drug delivery. BSA bonds with graphene non-covalently, thereby enabling the creation of a highly stable, non-aggregating aqueous graphene solution that may be stored in ambient conditions over extended periods.

In some embodiments, the pre-polymer solution further includes gelatin. In other embodiments, the pre-polymer solution is substantially free of gelatin. The gelatin can form any suitable proportion of the pre-polymer solution, such as about 0.5 mg/mL to about 10 mg/mL of the pre-polymer solution.

In some embodiments, the pre-polymer solution can include solvents in addition to water, such as polyethylene glycol (PEG). The PEG can form any suitable proportion of the pre-polymer solution, such as about 0.1 mg/mL to about 50 mg/mL, about 1 mg/mL to about 5 mg/mL, or about 2 mg/mL to about 3 mg/mL. PEG can reduce agglomeration of the graphene, and has both low toxicity and efficiency as a solvent for carbon-carbon bonds. In various embodiments, a microfluidic core-sheath technique for forming the fibers can include PEG in the core solution while the sheath solution is substantially free of PEG.

The polymerizing of the pre-polymer solution can include exposing the pre-polymer solution to a crosslinking solution. The crosslinking solution can be any suitable solution that induces crosslinking of the precursor for the biopolymer. For example, the crosslinking solution can include an aqueous $Ca^{2+}$ solution, and the precursor for the biopolymer can be alginate, with the biopolymer formed being calcium alginate. During the crosslinking, the $Ca^{2+}$ molecule can be diffused into the pre-polymer solution, thereby creating a calcium alginate encapsulating polymer matrix.

The polymerization can include injecting the pre-polymer solution into the crosslinking solution. The polymerization can include exposing the pre-polymer solution to the crosslinking solution in a microfluidic device. Performing the method using a microfluidic device can produce a hydrogel microfiber with highly tunable conductivity and mechanical properties.

The method can include forming a non-agglomerated aqueous solution of graphene. In order to fabricate a non-toxic aqueous solution of graphene, both chemical and mechanical manipulation of graphite can be used, such as exfoliation and fragmentation of graphite through sonication and magnetic stirring in BSA. Exfoliation may take the form of sonication, ultrasonics, ball milling, or a combination thereof.

Method of Using the Matrix-Encapsulated Cell

Various embodiments provide a method of using the matrix-encapsulated cell. The method can include detecting electrical signals from or sending electrical signals to (e.g., detecting, measuring, or a combination thereof) the one or more cells through the encapsulating polymer matrix. Detecting the electrical signals from the one or more cells can include detecting responses of the one or more cells to chemical or mechanical stimulus applied to the one or more cells.

EXAMPLES

Various embodiments of the present invention can be better understood by reference to the following Examples which are offered by way of illustration. The present invention is not limited to the Examples given herein.

Example 1. Preparation of Graphene Solution

A solution of 2% BSA, 5% Graphite, and water was prepared using ball mill. Similarly, a 0.1 mg/mL solution of graphene was fabricated through pure sonication. This graphene solution was used in the Examples herein.

In an alternative technique, a solution of 1,000 mg graphite and 500 mg BSA and water is prepared using a ball mill.

Example 2. Preparation of Alginate/Graphene/PEG Core Solution

3% Alginate and 2.5% PEG (w/v) was dissolved into the Graphene solution by magnetic stirring overnight at 800 rpm. The solution was sterilized via long-term exposure to UV radiation. Similarly, a solution of 40% Alginate and 10% Gelatin was used for extrusion encapsulations.

Example 3. Biocompatibility Test

To test the biocompatibility of the graphene solution, 200 µL were introduced into cells seeded onto a 6 well plate in 1 mL of media. These cells were observed for 48 hours.

Example 4. Fabrication of Microfluidic Devices

Microfluidic devices were created by curing PDMS on a photolithographic mold bearing the design. These PDMS halves were joined using plasma cleaning, and inlets were attached via glue.

Example 5. Fabrication of Alginate/Graphene/PEG Microfibers

Sheath solution was prepared with a concentration of 0.5% $CaCl_2$ and 5% PEG (w/v) in DI water. The core solution (i.e., the pre-polymer solution) was introduced into the center channel of the microfluidic device, while the sheath is pumped through the two outer channels. A syringe pump was used to maintain constant fluid velocity of 600:40 µL/min:µL/min (sheath:core). Resulting fibers were introduced into a 5% $CaCl_2$ water bath before collection. FIG. 1 illustrates a diagram of the microfluidic device.

The sheath solution traveled through the microfluidic device with the core solution, shaping it and helping to make sure it did not clog. An ionic transfer (e.g., calcium ions) from the sheath solution polymerized the core solution. As compared to extrusion, the microfluidic technique provided greater control over the shape and size of the fiber. The microfluidic technique may also help to align particles and bonds in a way that does not occur during an extrusion technique.

In an alternative technique, the flow rate ratio is 255:55 µL/min:µL/min (sheath:core). This flow rate ratio was used with a core solution of 3% alginate, 1.75% PEG, and 2.2% graphene. FIGS. 2(A)-(B) show scanning electron microscopy images of the generated fibers. FIG. 3 shows a plot showing fiber diameter versus flow rate ratio, showing both long and short diameters, since the cross-sectional area of the fiber was not perfectly round Example 6. Fabrication of Alginate/Graphene/Gelatin Extruded Microfibers Rat PC12 cells were introduced into the alginate/gelatin/graphene solution and were injected into a 10% $CaCl_2$ bath through a needle with an inner diameter of 0.013 mm. The resulting fibers were gathered and placed into 12 well plates for observation.

Example 7. Recovery of Encapsulated Cells

Cells were recovered by removing polymerized cell-laden alginate gels and placing them into 1 mL of 0.1 M PBS solution. Gels were gently aspirated, after which they were allowed to rest at 37° C. for 10 minutes. After one final aspiration, the resulting solution was centrifuged and the resulting cell suspension was plated.

Example 8. Mechanical Properties of Fibers

Fibers were created and mounted onto paper frames for transport. They were analyzed using an Instron Universal Testing Machine (Model 5569, Instron Engineering Corp., Canton, MA) with a 10 N load cell and an extension rate of 1 mm/min.

Example 9. Microscopy

Images were collected with an Axio Observer Z1 Inverted Microscope from Zeiss. Initial processing such as contrast and brightness were completed within the AxioVision Special Edition 64-bit software. Further processing, such as removal of debris outside of the well plate and compiling of fluorescent cell images, was completed within Adobe Photoshop CC 2018.

Example 10. SEM Images (SEM) analysis was performed using a JCM-6000 NeoScope Benchtop SEM with an accelerating voltage of 15 kV.

Example 11. Analysis of Results

Example 11.1. Biocompatibility of Graphene

Graphene introduced to cells seeded within six well plates did not cause any apparent sign of cellular distress. Cells were still adherent after 48 hours of graphene interaction, as seen in FIGS. 4(A)-(D), showing rat PC12 cells seeded onto 6 well plates observed at (A-B) 24 and (C-D) 48 hours after introduction of 200 μL of 5% Graphene solution.

Example 11.2. Encapsulation of Rat PC12 cells with Graphene

Rat PC12 cells were successfully encapsulated within graphene-laden alginate/gelatin fibers via the extrusion method, as seen in FIGS. 5(A)-(I), showing day 0 (A-C), day 3 (D-F), and day 7 (G-I); (A, D, G) non-polymerized control of alginate, gelatin, graphene and rat PC12 cells; (B, E, H) cells encapsulated in alginate fibers extruded in a 10% $CaCl_2$ bath from a needle with an inner diameter of 0.013 mm; and (C, F, I) cells which migrated from the hydrogels and attached on the surface of the well plate. Cells were observed migrating from within the fiber body to attach to the bottom of the well plates. This shows that cells survived the encapsulation process and maintained their ability to proliferate in standard conditions. Likewise, the unpolymerized alginate/graphene control (A, D, G) further show the biocompatibility of graphene over a seven-day process.

Figure 6:
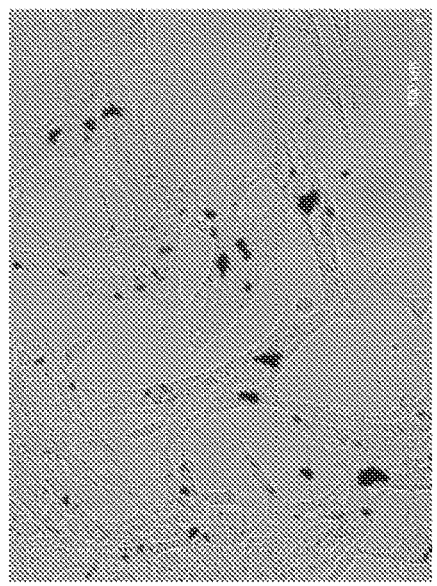
FIG. 6 illustrates cells recovered from encapsulation within 40% alginate, 10% gelatin and 1 mg/mL graphene gels after one week, with a scale bar is 100 microns, in accordance with various embodiments.

Cells encapsulated in this way were successfully recovered after one week, as seen in FIG. 6. Cells survived within the polymer, and upon recovery showed the ability to adhere to the surface of well plates and proliferate. Cells maintained standard morphologies.

Figure 7C:
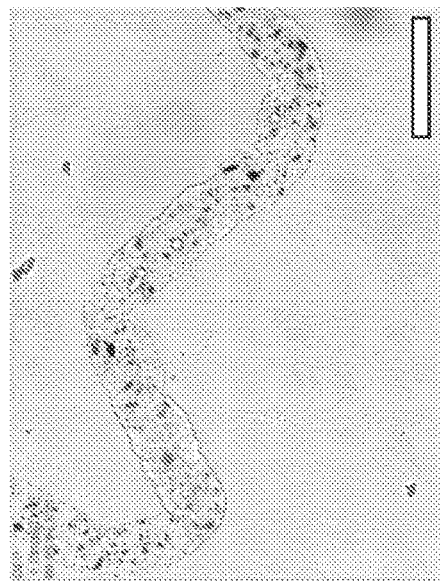
FIGS. 7(A)-(C) illustrate fibers made with alginate, graphene, and cells within a Microfluidic device with a flow rate ratio of 600:40 μL/min:μL/min (sheath:core), in accordance with various embodiments. Cells were stained with GPA fluorescent proteins (A), imaged in brightfield (B), and the images were combined (C). Scale bars represent 100 microns.
Figure 7B:
Figure 7A:

Example 11.3. Microfluidic encapsulation of Rat PC12 cells in Graphene/Alginate Solutions Cells and graphene were successfully encapsulated within Alginate fibers using a microfluidic device. FIGS. 7(A)-(C) illustrate fibers made with alginate, graphene, and cells within a microfluidic device with a flow rate ratio of 600:40 μL/min:μL/min (sheath:core). Cells were stained with GPA fluorescent proteins (A), imaged in brightfield (B), and the images were combined (C). Scale bars represent 100 microns.

Example 11.4. Characterization of Fibers

Figure 8A:
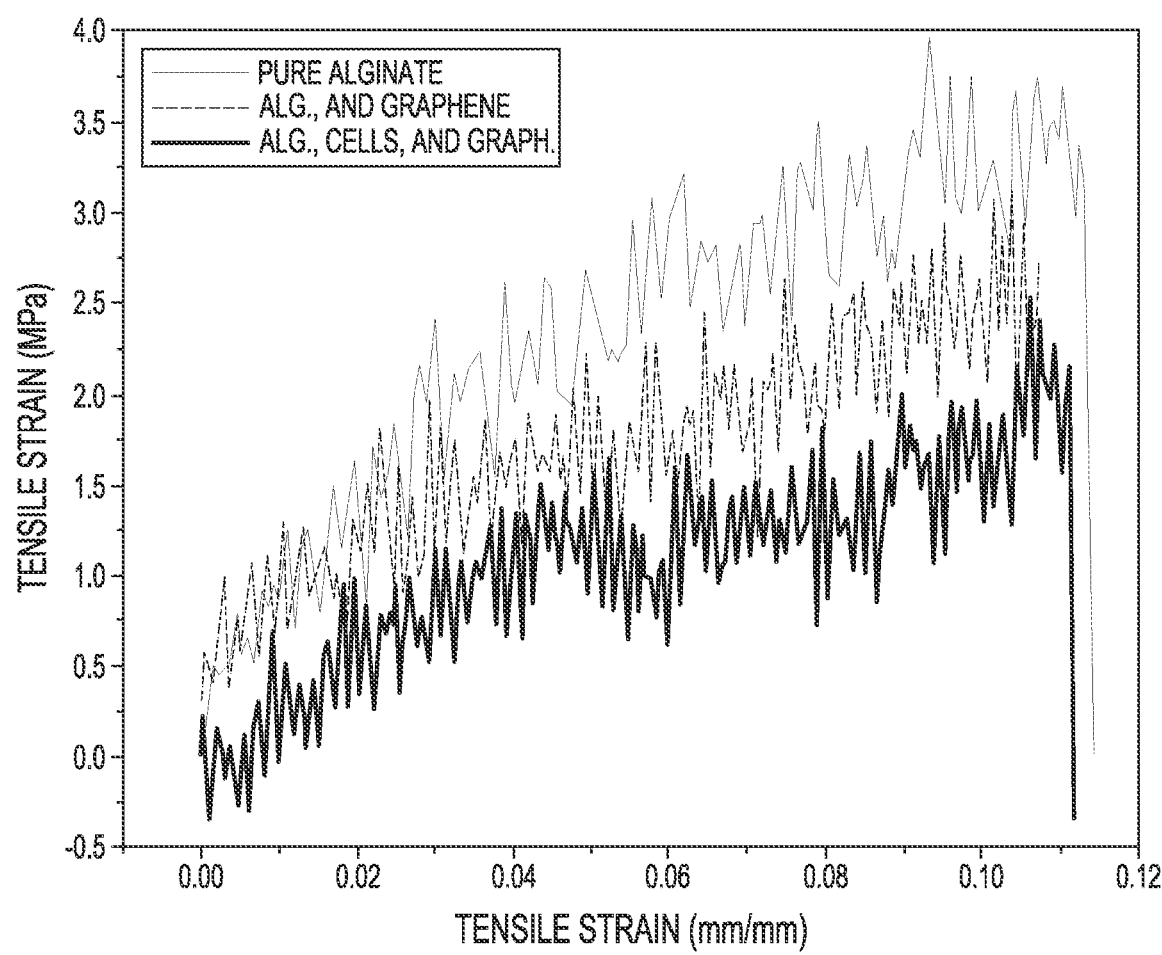
FIG. 8(A) shows tensile stress versus tensile strain for pure alginate, alginate and graphene, and for alginate/cells/graphene, in accordance with various embodiments.
Figure 8B:
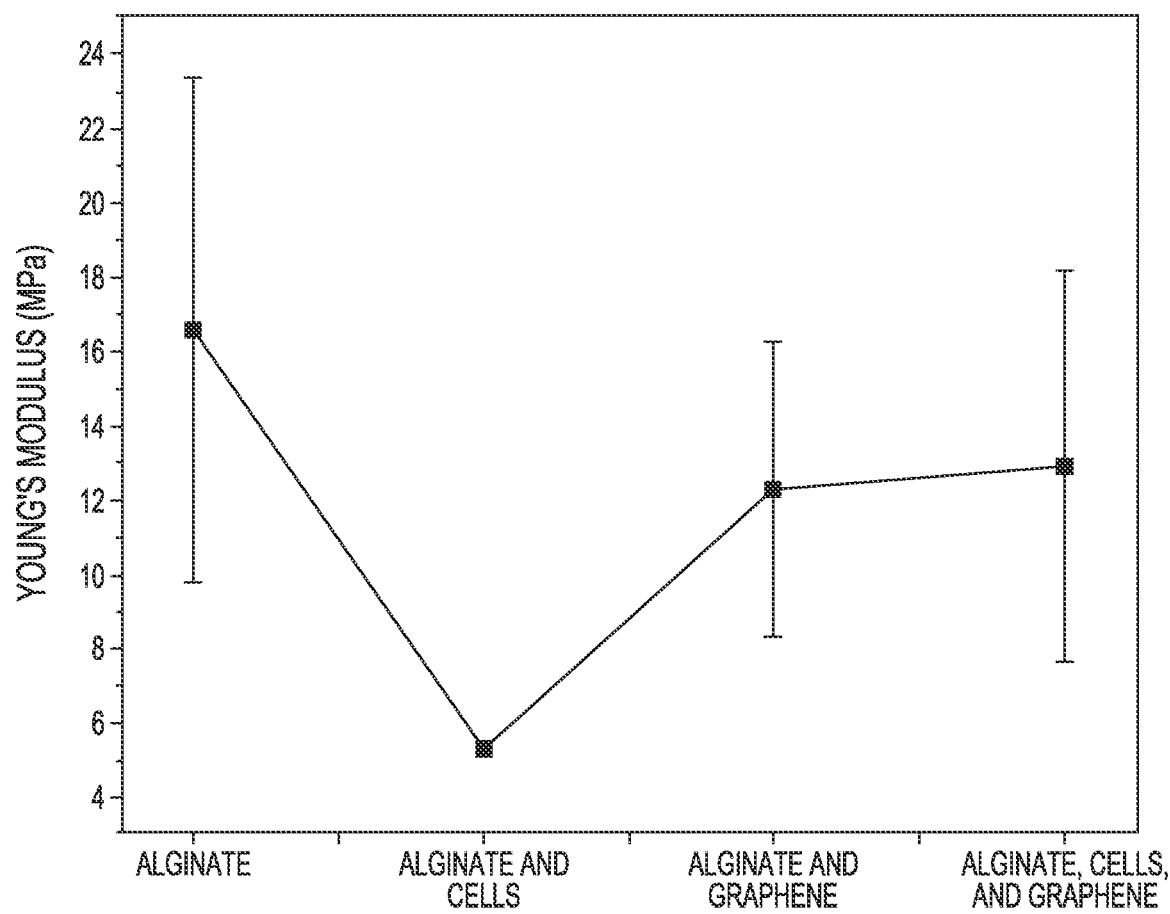
FIG. 8(B) shows the Young's modulus for alginate, alginate and cells, alginate and graphene, and for alginate/cells/graphene, in accordance with various embodiments.

Fibers were characterized and their elastic moduli were calculated. Preliminary data shows minor differences in the mechanical properties of fibers made with pure alginate fibers, alginate and graphene fibers, and alginate/graphene fibers with encapsulated cells. FIG. 8(A) shows tensile stress versus tensile strain for pure alginate, alginate and graphene, and for alginate/cells/graphene. FIG. 8(B) shows the Young's modulus for alginate, alginate and cells, alginate and graphene, and for alginate/cells/graphene. Preliminary results of adding graphene and cells to microfluidically created 1.5% alginate fibers in a 5% $CaCl_2$ bath and a flow rate ratio of 225:10 μL/min (sheath:core) showed that these factors do not affect mechanical properties.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Embodiment 1 provides a matrix-encapsulated cell comprising:
an encapsulating polymer matrix comprising a biopolymer and graphene; and
one or more of the cells encapsulated within the encapsulating polymer, wherein the graphene directly contacts at least some of the cells;
wherein the matrix encapsulating the one or more cells is electrically conductive.

Embodiment 2 provides the matrix-encapsulated cell of Embodiment 1, wherein the encapsulating polymer matrix is a fiber, a fibrous mat, a membrane, or a film.

Embodiment 3 provides the matrix-encapsulated cell of any one of Embodiments 1-2, wherein the encapsulating polymer matrix is a fiber.

Embodiment 4 provides the matrix-encapsulated cell of any one of Embodiments 1-3, wherein the biopolymer comprises gelatin, chitosan, polycaprolactone, alginate, a polysaccharide, or a combination thereof.

Embodiment 5 provides the matrix-encapsulated cell of any one of Embodiments 1-4, wherein the biopolymer comprises a polysaccharide.

Embodiment 6 provides the matrix-encapsulated cell of any one of Embodiments 1-5, wherein the biopolymer comprises calcium alginate.

Embodiment 7 provides the matrix-encapsulated cell of any one of Embodiments 1-6, wherein the biopolymer is about 1 mg/mL to about 5 mg/mL of the encapsulating polymer matrix.

Embodiment 8 provides the matrix-encapsulated cell of any one of Embodiments 1-7, wherein the encapsulating polymer matrix is substantially free of graphene oxide.

Embodiment 9 provides the matrix-encapsulated cell of any one of Embodiments 1-8, wherein the encapsulating polymer matrix is substantially free of reduced oxidized graphene.

Embodiment 10 provides the matrix-encapsulated cell of any one of Embodiments 1-9, wherein the graphene is homogeneously distributed in the encapsulating polymer matrix.

Embodiment 11 provides the matrix-encapsulated cell of any one of Embodiments 1-10, wherein the graphene is about 10 mg/mL to about 25 mg/mL of the combination of the encapsulating polymer matrix and the one or more cells.

Embodiment 12 provides the matrix-encapsulated cell of any one of Embodiments 1-11, wherein the graphene provides the electrical conductivity of the fiber.

Embodiment 13 provides the matrix-encapsulated cell of any one of Embodiments 1-12, wherein the one or more cells are one or more living cells.

Embodiment 14 provides the matrix-encapsulated cell of any one of Embodiments 1-13, wherein the one or more cells comprise rat PC12 cells, mouse astrocyte cells (MACs), adult hippocampal progenitor stem cells (AHPCs), or mesenchymal stem cells (MSCs).

Embodiment 15 provides the matrix-encapsulated cell of any one of Embodiments 1-14, wherein the one or more cells comprise mammalian cells.

Embodiment 16 provides the matrix-encapsulated cell of any one of Embodiments 1-15, wherein the one or more cells are about $1\times10^4$ cells/mL to about $1\times10^8$ cells/mL of the combination of the encapsulating polymer matrix and the one or more cells.

Embodiment 17 provides the matrix-encapsulated cell of any one of Embodiments 1-16, wherein the one or more cells are about $1\times10^6$ cells/mL to about $5\times10^6$ cells/mL of the combination of the encapsulating polymer matrix and the one or more cells.

Embodiment 18 provides the matrix-encapsulated cell of any one of Embodiments 1-17, wherein the one or more cells comprise rat PC12 cells.

Embodiment 19 provides the matrix-encapsulated cell of any one of Embodiments 1-18, wherein the encapsulating matrix further comprises gelatin.

Embodiment 20 provides the matrix-encapsulated cell of any one of Embodiments 1-19, wherein the encapsulating matrix further comprises a surfactant.

Embodiment 21 provides the matrix-encapsulated cell of Embodiment 20, wherein the surfactant comprises polyoxyethylene (20) sorbitan monolaurate, polyoxyethylene (20) sorbitan monopalmitate, polyoxyethylene (20) sorbitan monostearate, or polyoxyethylene (20) sorbitan monooleate), polyethylene glycol (PEG), bovine serum albumen (BSA), or a combination thereof.

Embodiment 22 provides the matrix-encapsulated cell of any one of Embodiments 20-21, wherein the surfactant comprises bovine serum albumen (BSA).

Embodiment 23 provides the matrix-encapsulated cell of any one of Embodiments 1-22, wherein the encapsulating matrix further comprises PEG.

Embodiment 24 provides the matrix-encapsulated cell of any one of Embodiments 3-23, wherein the fiber has a diameter of about 1 micron to about 100 microns.

Embodiment 25 provides the matrix-encapsulated cell of any one of Embodiments 3-24, wherein the fiber has a diameter of about 10 microns to about 25 microns.

Embodiment 26 provides a fiber comprising:
an encapsulating polymer matrix comprising a biopolymer and graphene; and
one or more cells encapsulated within the encapsulating polymer, wherein the graphene directly contacts at least some of the cells;
wherein the matrix encapsulating the one or more cells is electrically conductive.

Embodiment 27 provides a method of making the matrix-encapsulated cell of any one of Embodiments 1-25, the method comprising:
polymerizing a pre-polymer solution, the pre-polymer solution comprising
the one or more cells,
the graphene, and
a precursor for the biopolymer.

Embodiment 28 provides the method of Embodiment 27, wherein the graphene is about 10 mg/mL to about 30 mg/mL of the pre-polymer solution.

Embodiment 29 provides the method of any one of Embodiments 27-28, wherein the precursor for the biopolymer is about 2 mg/mL to about 8 mg/mL of the pre-polymer solution.

Embodiment 30 provides the method of any one of Embodiments 27-29, wherein the pre-polymer solution further comprises a surfactant to maintain the graphene in a non-agglomerated state during the polymerization.

Embodiment 31 provides the method of Embodiment 30, wherein the surfactant is about 5 mg/mL to about 15 mg/mL of the pre-polymer solution.

Embodiment 32 provides the method of any one of Embodiments 27-31, wherein the pre-polymer solution further comprises gelatin.

Embodiment 33 provides the method of Embodiment 32, wherein the gelatin is about 0.5 mg/mL to about 10 mg/mL of the pre-polymer solution.

Embodiment 34 provides the method of any one of Embodiments 27-33, wherein the pre-polymer solution further comprises PEG.

Embodiment 35 provides the method of any one of Embodiments 27-34, wherein the polymerizing comprises exposing the pre-polymer solution to a crosslinking solution.

Embodiment 36 provides the method of Embodiment 35, wherein the crosslinking solution comprises an aqueous $Ca^{2+}$ solution.

Embodiment 37 provides the method of any one of Embodiments 35-36, wherein the polymerization comprises injecting the pre-polymer solution into the crosslinking solution.

Embodiment 38 provides the method of any one of Embodiments 35-37, wherein the polymerization comprises exposing the pre-polymer solution to the crosslinking solution in a microfluidic device.

Embodiment 39 provides a method of using the matrix-encapsulated cell of any one of Embodiments 1-25, the method comprising:
detecting electrical signals from or sending electrical signals to the one or more cells through the encapsulating polymer matrix.

Embodiment 40 provides the method of Embodiment 39, wherein detecting the electrical signals from the one or more cells comprises detecting responses of the one or more cells to chemical or mechanical stimulus applied to the one or more cells.

Embodiment 41 provides the matrix-encapsulated cell, fiber, or method of any one or any combination of Embodiments 1-40 optionally configured such that all elements or options recited are available to use or select from.

What is claimed is:

1. A method of making one or more matrix-encapsulated cells, the method comprising:
polymerizing a pre-polymer solution to form the one or more matrix-encapsulated cells, the pre-polymer solution comprising
one or more cells,
graphene, and
a precursor for a biopolymer, wherein the one or more matrix-encapsulated cells comprise an encapsulating polymer matrix comprising the biopolymer and the graphene, wherein the graphene directly contacts at least some of the one or more cells, wherein the encapsulating polymer matrix is electrically conductive, and wherein the encapsulating polymer matrix is a fiber having a shape that has a diameter of about 1 micron to about 100 microns and a length that is at least about 1 cm; and wherein the polymerizing comprises
injecting the pre-polymer solution into a crosslinking solution in the shape of the fiber, or
microfluidically exposing the pre-polymer solution as a core solution to the crosslinking solution as a sheath solution having the shape of the fiber.

2. The method of claim 1, wherein the graphene is about 10 mg/mL to about 30 mg/mL of the pre-polymer solution.

3. The method of claim 1, wherein the precursor for the biopolymer is about 2 mg/mL to about 8 mg/mL of the pre-polymer solution.

4. The method of claim 1, wherein the pre-polymer solution further comprises a surfactant.

5. The method of claim 4, wherein the surfactant is about 5 mg/mL to about 15 mg/mL of the pre-polymer solution.

6. The method of claim 4, wherein the surfactant comprises a polysorbate-type nonionic surfactant formed by the ethoxylation of sorbitan before addition of a long-chain fatty acid, polyethylene glycol (PEG), bovine serum albumen (BSA), or a combination thereof.

7. The method of claim 4, wherein the surfactant maintains the graphene in a non-agglomerated state during the polymerizing.

8. The method of claim 1, wherein the pre-polymer solution further comprises gelatin.

9. The method of claim 8, wherein the gelatin is about 0.5 mg/mL to about 10 mg/mL of the pre-polymer solution.

10. The method of claim 1, wherein the pre-polymer solution further comprises PEG.

11. The method of claim 1, wherein the crosslinking solution comprises an aqueous $Ca^{2+}$ solution.

12. The method of claim 1, wherein the polymerizing comprises the injecting of the pre-polymer solution into the crosslinking solution.

13. The method of claim 1, wherein the polymerizing comprises the microfluidically exposing the pre-polymer solution to the crosslinking solution, wherein the polymerizing is performed in a microfluidic device.

14. The method of claim 1, wherein the biopolymer comprises gelatin, chitosan, polycaprolactone, alginate, a polysaccharide, or a combination thereof.

15. The method of claim 1, wherein the biopolymer comprises calcium alginate.

16. The method of claim 1, wherein the encapsulating polymer matrix is less than or equal to 1 wt % graphene oxide and wherein the encapsulating polymer matrix is less than or equal to 1 wt % reduced oxidized graphene.

17. The method of claim 1, wherein the one or more cells are one or more living cells.

18. The method of claim 1, wherein the length of the fiber is about 1 cm to about 1 m.

* * * * *